United States Patent [19]

Grabiak

[11] 4,250,320

[45] Feb. 10, 1981

[54] PROCESS FOR PRODUCING SUBSTITUTED BENZOXAPHOSPHOLES

[75] Inventor: Raymond C. Grabiak, Creve Coeur, Mo.

[73] Assignee: Monsanto Company, St. Louis, Mo.

[21] Appl. No.: 55,433

[22] Filed: Jul. 6, 1979

[51] Int. Cl.³ .............................. C07F 9/02; C07F 7/08
[52] U.S. Cl. ..................................... 556/404; 260/968
[58] Field of Search ................. 260/936, 968; 556/404

[56] References Cited

U.S. PATENT DOCUMENTS

| | | | |
|---|---|---|---|
| 2,916,510 | 12/1959 | Garner | 260/936 |
| 4,102,949 | 7/1978 | Schliebs et al. | 260/936 |

OTHER PUBLICATIONS

Collins, et al., "Aust. J. Chem.," vol. 27, (1974), pp. 1759–1765.
Dennis, et al., "J.A.C.S.," vol. 88, (1966), p. 3431.
Dannley, et al., "J. Org. Chem.," vol. 26, (1961), p. 3995.
Ludt, et al., "J. Org. Chem.," vol. 36, (1971), p. 1607.
Hellwinkel, et al., "Tetrahedron Letters," vol. 37, (1977), pp. 3241–3244.
Eberhard, et al., "J.A.C.S.," vol. 87, (1965), p. 253.

*Primary Examiner*—Anton H. Sutto
*Attorney, Agent, or Firm*—Patricia A. Coburn; Donald W. Peterson

[57] ABSTRACT

This disclosure relates to a process for producing substituted benzoxaphospholes employing a directive metalation technique utilizing an organolithium compound. The substituted benzoxaphospholes produced are useful as herbicides.

3 Claims, No Drawings

PROCESS FOR PRODUCING SUBSTITUTED BENZOXAPHOSPHOLES

This invention relates to a process for the production of substituted benzoxaphospholes which are useful as herbicides.

In accordance with the present invention, substituted benzoxaphospholes of the formula

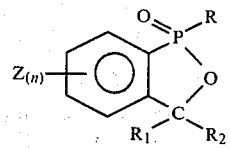
(I)

wherein R is selected from the group consisting of lower alkyl, lower alkoxy, $C_3$–$C_8$ cycloalkyl, phenyl, biphenyl, phenoxyphenyl and substituted phenyl containing from one to three substituents individually selected from the class consisting of lower alkyl, lower alkoxy, lower dialkylamino, diphenylamino, $C_3$–$C_8$ cycloalkyl, fluoro, chloro, trifluoromethyl and trimethylsilyl; $R_1$ and $R_2$ are independently selected from the group consisting of hydrogen, lower alkyl, $C_3$–$C_8$ cycloalkyl, and phenyl; Z is selected from the group consisting of lower alkyl, lower alkoxy, phenyl, phenoxy, lower dialkylamino, diphenylamino, $C_3$–$C_8$ cycloalkyl, fluoro, chloro, trifluoromethyl and trimethylsilyl; n is an integer from 0 to 2; are produced by forming an admixture consisting essentially of a substituted benzyl phosphonate of the formula

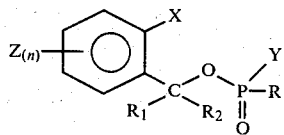
(II)

wherein R, $R_1$, $R_2$, Z and n are above defined; X is bromo or iodo and Y is lower alkoxy; and an organolithium compound in the presence of an aprotic solvent within a temperature range of $-80°$ C. to $-65°$ C.

It is believed that the reaction takes place in accordance with the following reaction scheme which employs t-butyllithium for illustrative purposes as the organolithium compound:

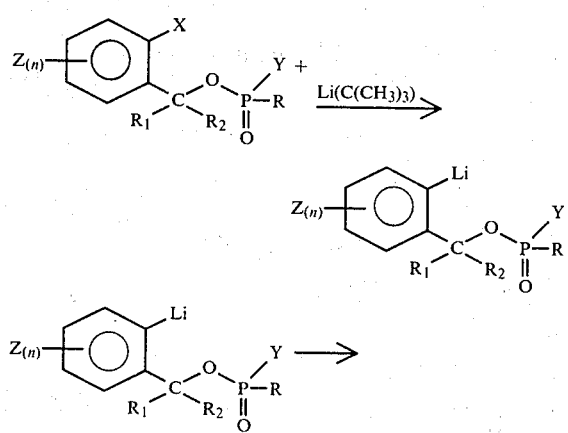

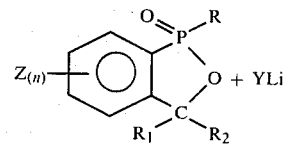

In conducting the process of this invention, the temperature of the reaction can be from $-80°$ C. to $-65°$ C. It is generally preferred to conduct the process within a temperature range of $-76°$ C. to $-70°$ C. Temperatures greater than $-65°$ C. give rise to a multitude of by-products and give low yields of the substituted benzoxaphospholes which are difficult to recover.

The ratio of reactants, that is the substituted phosphonate and the organolithium compound, is not narrowly critical. As is apparent from the above equation, to obtain good yields and for ease of recovery of the desired product, one should employ one mole of the organolithium compound for each mole of the substituted phosphonate. For best yields and ease of recovery of the desired product, a ratio of the organolithium compound to the substituted phosphonate of 2:1 is preferred. Ratios higher than 2:1 can be employed but no commensurate advantages are obtained thereby, since at higher ratios, excess organolithium compound would have to be removed before product recovery. At ratios lower than 1:1, product isolation becomes difficult.

Due to the reactive nature of the various intermediates and reactants, the process of the present invention is conducted in an aprotic solvent under essentially anhydrous conditions and in an inert atmosphere. Illustrative of the aprotic solvents employed in the process of this invention include cyclohexane, methylcyclohexane, hexane, benzene, octane, diethyl ether, tetrahydrofuran, and the like.

The process of this invention can be conducted at atmospheric, sub-atmospheric or super-atmospheric pressure. For convenience and economy, it is generally preferred to conduct these processes at atmospheric pressure.

Illustrative of the organolithium compounds employed in the process of this invention include alkyllithiums such as ethyllithium, butyllithium, t-butyllithium and aryllithiums such as phenyllithium and the like.

As employed herein, the terms "lower alkyl" and "lower alkoxy" designate alkyl and alkoxy radicals which have up to six carbon atoms in a straight or branched chain. Groups representative of these radicals include, for example, methyl, ethyl, propyl, isopropyl, butyl, isobutyl, t-butyl, n-hexyl, methoxy, ethoxy, propoxy, isopropoxy, butoxy, hexoxy and the like.

Illustrative of the cycloalkyl substituents are groups such as cyclopropyl, cyclobutyl, cyclopentyl, cyclohexyl, cyclooctyl and the like.

Illustrative of the substituted phenyl groups which R and $R_1$ represent are mono-substituted phenyl wherein the substituent is in the ortho, meta or para position, for example, methylphenyl, butylphenyl, methoxyphenyl, butoxyphenyl, fluorophenyl, chlorophenyl, trifluoromethylphenyl, dimethylaminophenyl, methylethylaminophenyl and the like and the di- and tri-substituted phenyl groups wherein the substituents are the same or different and are located in the 2, 3, 4, 5 or 6 positions of the phenyl ring, for example, dichlorophenyl, difluorophenyl, methylchlorophenyl, butoxyfluorophenyl, methylbutylphenyl, methoxybutoxyphenyl, dimethoxyphenyl, methylphenoxyphenyl, trichlorophenyl, trimethylphenyl, tributoxyphenyl and the like.

The substituted benzoxaphospholes of formula (I) are useful as herbicides.

The phosphonates of formula (II) used as the starting materials in the production of the compounds of this invention are prepared employing the following procedure.

Under anhydrous conditions, a solution containing a phosphonate ester of the formula

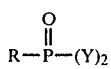

wherein R and Y are above defined, in carbon tetrachloride is treated with phosphorus pentachloride at 0° C. The reaction mixture is stirred for one hour at 0° C., then for 16 hours at 26° C. The resulting mixture is concentrated in vacuo and the residue distilled to yield a phosphonic chloride ester of the formula

A solution containing the phosphonic chloride ester in anhydrous ether is slowly added over a period of one hour to a substituted benzyl alcohol of the formula

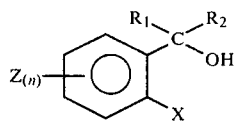

wherein $R_1$ and X are above defined; in the presence of 1,5-diazabicyclo-[5.4.0]undec-5-ene in anhydrous ether at 0° C. producing a suspension which is stirred at 26° C. for one hour and filtered. The ether filtrate is washed with water, then 5% hydrochloric acid, dried over magnesium sulfate and concentrated in vacuo to yield an oil. This oil is distilled under high vacuum to yield the phosphonate of formula (I).

The following illustrative, non-limiting examples will serve to further demonstrate to those skilled in the art the manner in which the specific compounds within the scope of this invention can be prepared. In the examples, all parts are parts by weight unless otherwise expressly stated.

EXAMPLE 1

Under a nitrogen atmosphere a solution of ethyl-2-bromophenyl-3-trifluoromethylphenylphosphonate (2.4 g, 0.00567 mole) in 50 ml. of tetrahydrofuran was cooled to −76° C. by means of a solid carbon dioxide-acetone bath. To the cooled solution was dropwise added a solution of t-butyllithium (0.74 g, 0.0116 mole) in 6.1 ml. of pentane at a rate such that the temperature of the reaction was maintained below −65° C. The reaction mixture was then stirred for one hour at −76° C. after which time the reaction mixture was allowed to increase to 26° C. over a period of 45 minutes. The reaction was quenched with the addition of 1 ml. of acetic acid. The reaction mixture was concentrated under vacuum to yield a yellow residue which was partitioned between methylene chloride and water. The methylene chloride layer was dried over magnesium sulfate and concentrated in vacuo to yield a yellow glass residue. The yellow residue was distilled in a Kugelrohr at 130° C. and 0.2 mm to produce a colorless oil which was crystallized upon trituration in petroleum ether to yield 1-[3-(trifluoromethyl)phenyl]-1,3-dihydro-2,1-benzoxaphosphole-1-oxide (0.85 g, 51% yield) as a white solid having a melting point of 102°–106° C. and the following analysis:

Calculated: C, 56.39; H, 3.38.
Found: C, 56.41; H, 3.46.

EXAMPLE 2

Under a nitrogen atmosphere a solution of ethyl-2-bromophenyl-3-trifluoromethylphenyl phosphonate (4.2 g, 0.010 mol) in 50 ml. of ether was cooled to −72° C. by means of a solid carbon dioxide-acetone bath. To the cooled solution was dropwise added a solution of n-butyllithium (0.64 g, 0.010 mol) in hexane and ether over a period of 18 minutes. The reaction mixture was then stirred for 0.5 hours at −72° C. after which time the temperature of the reaction mixture was allowed to increase to 26° C. The reaction mixture was added to 100 ml. of 5% hydrochloric acid and the organic layer was separated, washed with 5% hydrochloric acid, dried over magnesium sulfate and then concentrated in vacuo to yield a pale yellow oil. To this oil was added 10 ml. of 10% perchloric acid and the resulting mixture was heated at reflux for one hour. The reaction mixture was cooled and then added to methylene chloride. The methylene chloride layer was separated, washed with water, then 5% sodium bicarbonate, dried over magnesium sulfate and concentrated in vacuo to yield a yellow oil. This oil was distilled at 150° C. and 0.1 torr to yield a colorless oil. The oil was suspended in 5 ml. of concentrated hydrochloric acid and then refluxed for one hour. The suspension was cooled and then partitioned between methylene chloride and water. The methylene chloride layer was washed with water, with 5% sodium bicarbonate, again with water, dried over magnesium sulfate and then concentrated in vacuo to yield an oil. This oil was distilled at 80° C. and 0.2 torr to remove any by-products and then distilled at 130° C. and 0.2 torr to yield a colorless oil. This oil was suspended in petroleum ether to yield after cooling the ether suspension 1-[3-(trifluoromethyl)phenyl]-1,3-dihydro-2,1-benzoxaphosphole-1-oxide (0.1 g, 3.5% yield) as white flakes having a melting point of 102°–106° C.

Other compounds which may be prepared employing the process of the present invention include, for example, 1-ethyl-1,3-dihydro-2,1-benzoxaphosphole-1-oxide;
1-ethoxy-3-methyl-1,3-dihydro-2,1-benzoxaphosphole-1-oxide;
1-cyclohexyl-3-phenyl-1,3-dihydro-2,1-benzoxaphosphole-1-oxide;
1-phenyl-3-butyl-1,3-dihydro-2,1-benzoxaphosphole-1-oxide;
1-(4-dimethylaminophenyl)-1,3-dihydro-2,1-benzoxaphosphole-1-oxide;
1-(3-fluorophenyl)-3-propyl-1,3-dihydro-2,1-benzoxaphosphole-1-oxide;
1-(2,4-dichlorophenyl)-3-diethyl-1,3-dihydro-2,1-benzoxaphosphole-1-oxide;
1-(2-methylphenyl)-1,3-dihydro-2,1-benzoxaphosphole-1-oxide; and 1-(2,4-diethoxyphenyl)-3-cyclohexyl-1,3-dihydro-2,1-benzoxaphosphole-1-oxide.

What is claimed is:

1. A process for producing a compound of the formula

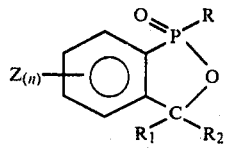

wherein R is selected from the group consisting of lower alkyl, lower alkoxy, $C_3$–$C_8$ cycloalkyl, phenyl, biphenyl, phenoxyphenyl and substituted phenyl containing from one to three substituents individually selected from the class consisting of lower alkyl, lower alkoxy, lower dialkylamino, diphenylamino, $C_3$–$C_8$ cycloalkyl, fluoro, chloro, trifluoromethyl and trimethylsilyl; $R_1$ and $R_2$ are independently selected from the group consisting of hydrogen, lower alkyl, $C_3$–$C_8$ cycloalkyl, and phenyl; Z is selected from the group consisting of lower alkyl, lower alkoxy, phenyl, phenoxy, lower dialkylamino, diphenylamino, $C_3$–$C_8$ cycloalkyl, fluoro, chloro, trifluoromethyl and trimethylsilyl; n is an integer from 0 to 2; which comprises forming an admixture consisting essentially of a substituted benzyl phosphonate of the formula

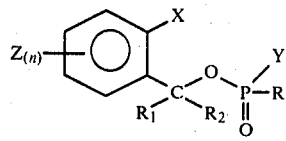

wherein R, $R_1$, $R_2$, Z and n are above defined; X is bromo or iodo and Y is lower alkoxy; and an organolithium compound selected from the group consisting of alkyllithiums and aryllithiums in the presence of an aprotic solvent within a temperature range of $-80°$ C. to $-65°$ C.

2. A process according to claim 1 wherein the organolithium compound is t-butyllithium.

3. A process according to claim 1 wherein the aprotic solvent is tetrahydrofuran.